United States Patent
Lim et al.

(10) Patent No.: US 10,694,952 B2
(45) Date of Patent: Jun. 30, 2020

(54) ELECTRONIC DEVICE

(71) Applicant: LG ELECTRONICS INC., Seoul (KR)

(72) Inventors: Gueisam Lim, Seoul (KR); Yongju Yang, Seoul (KR); Kyuhyoung Choi, Seoul (KR); Haeseok Eo, Seoul (KR); Dongwon Kim, Seoul (KR); Heejin Park, Seoul (KR); Sanghun Kim, Seoul (KR); Seungwoo Shin, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 257 days.

(21) Appl. No.: 15/736,987

(22) PCT Filed: Jun. 1, 2016

(86) PCT No.: PCT/KR2016/005806
§ 371 (c)(1),
(2) Date: Dec. 15, 2017

(87) PCT Pub. No.: WO2016/204432
PCT Pub. Date: Dec. 22, 2016

(65) Prior Publication Data
US 2018/0168456 A1    Jun. 21, 2018

(30) Foreign Application Priority Data
Jun. 16, 2015 (KR) .................. 10-2015-0084841

(51) Int. Cl.
*A61B 5/00* (2006.01)
*G02B 27/48* (2006.01)
*G16H 40/63* (2018.01)

(52) U.S. Cl.
CPC .......... *A61B 5/0077* (2013.01); *A61B 5/0002* (2013.01); *A61B 5/0064* (2013.01);
(Continued)

(58) Field of Classification Search
CPC ........ G16H 40/63; G02B 27/48; A61B 5/444; A61B 5/442; A61B 5/0077; A61B 5/0064;
(Continued)

(56) References Cited

U.S. PATENT DOCUMENTS

| 7,978,259 B2 * | 7/2011 | Matsuo | G06K 9/00033 348/370 |
|---|---|---|---|
| 2005/0154382 A1 * | 7/2005 | Altshuler | A61B 18/203 606/9 |

(Continued)

FOREIGN PATENT DOCUMENTS

| JP | 11-332879 A | 12/1999 |
|---|---|---|
| JP | 2001-259056 A | 9/2001 |

(Continued)

*Primary Examiner* — Bo Joseph Peng
(74) *Attorney, Agent, or Firm* — Birch, Stewart, Kolasch & Birch, LLP

(57) ABSTRACT

An electronic device is disclosed. The electronic device of the present invention comprises a body; a head being extended from the body, the head including an internal space for accommodating; a light transmission circle being formed on the head; and a measurement module being installed in the internal space of the head, the measurement module facing the light transmission circle, wherein the measurement module includes: a plurality of first light source providing the light transmission circle with light for speckle imaging; a image sensor being positioned between the light transmission circle and the plurality of first light sources, the image sensor being spaced apart from the plurality of first light sources, the image sensor facing the light transmission
(Continued)

circle; and a lens covering the image sensor, the lens being positioned between the image sensor and the light transmission circle.

10 Claims, 31 Drawing Sheets

(52) U.S. Cl.
CPC .............. *A61B 5/442* (2013.01); *A61B 5/444* (2013.01); *A61B 5/743* (2013.01); *A61B 5/7435* (2013.01); *A61B 5/7445* (2013.01); *G02B 27/48* (2013.01); *G16H 40/63* (2018.01); *A61B 5/0022* (2013.01); *A61B 5/6898* (2013.01); *A61B 5/744* (2013.01); *A61B 2560/0431* (2013.01); *A61B 2562/0233* (2013.01)

(58) Field of Classification Search
CPC ... A61B 5/7445; A61B 5/7435; A61B 5/0002; A61B 5/743; A61B 5/0022; A61B 5/6898; A61B 5/744; A61B 2560/0431; A61B 2562/0233

See application file for complete search history.

(56) References Cited

U.S. PATENT DOCUMENTS

| | | | |
|---|---|---|---|
| 2008/0123106 A1 | 5/2008 | Zeng et al. |
| 2011/0159463 A1 | 6/2011 | Samain |
| 2012/0162438 A1 | 6/2012 | Thakor et al. |

FOREIGN PATENT DOCUMENTS

| | | |
|---|---|---|
| JP | 2005-168894 A | 6/2005 |
| KR | 10-2005-0005728 A | 1/2005 |
| KR | 10-2013-0005598 A | 1/2013 |
| KR | 10-1444940 B1 | 9/2014 |
| WO | WO 2014/151114 A1 | 9/2014 |

* cited by examiner (a)

(b)

(c)

(d)

(e)

(a)

(b)

(c)

(d)

(a)

(b)

(c)

(d)

(a)　　　　　(b)

(c)　　　　　(d)

(e)　　　(f)　　　(g)

ELECTRONIC DEVICE

CROSS REFERENCE TO RELATED APPLICATIONS

This application is the National Phase of PCT International Application No. PCT/KR2016/005806, filed on Jun. 1, 2016, which claims priority under 35 U.S.C. 119(a) to Patent Application No. 10-2015-0084841, filed in Republic of Korea on Jun. 16, 2015, all of which are hereby expressly incorporated by reference into the present application.

TECHNICAL FIELD

The present invention relates to an electronic device. In particular, the present invention relates to an electronic device capable of measuring skin conditions.

BACKGROUND ART

Recently, interest in skin has been increasing. In general, dermatologic care and procedures are expensive. In addition, since it is difficult to accurately measure or diagnose the condition of the user's own skin, side effects are often caused by using cosmetics which are not suitable for the user.

The condition of the skin can be evaluated by various factors. Factors such as skin elasticity, oiliness (or oil), moisture, and wrinkles can be some criteria for assessing the condition of the skin. You can manage your own skin if you know the accurate measurement of your skin or history of your skin.

Conventional skin measurement devices have problems in that they are big sized suitable for a clinic for skin, or in that they have low accuracy for skin measurement if they are small.

To support and enhance the functionality of such electronic devices, it may be considered to improve the structure and/or software of the electronic device.

DISCLOSURE

Technical Problem

The present invention is to solve the above-mentioned problems and other problems. Another object of the present invention is to precisely measure the skin condition of the user.

Another object of the present invention is to provide a laser light for speckle imaging.

Another object of the present invention is to improve the image for skin measurement.

Another object of the present invention is to measure a skin condition of the user and to provide the user with a suitable care.

Another object of the present invention is to share information on measured skin condition with other electronic devices.

Technical Solution

According to an aspect of the present invention, there is provided an electronic device comprising a body; a head being extended from the body, the head including an internal space for accommodating; a light transmission circle being formed on the head; and a measurement module being installed in the internal space of the head, the measurement module facing the light transmission circle, wherein the measurement module includes: a plurality of first light source providing the light transmission circle with light for speckle imaging; a image sensor being positioned between the light transmission circle and the plurality of first light sources, the image sensor being spaced apart from the plurality of first light sources, the image sensor facing the light transmission circle; and a lens covering the image sensor, the lens being positioned between the image sensor and the light transmission circle.

According to another aspect of the present invention, the electronic device may further comprises a second light source providing the light transmission circle with light for photographing an image.

According to another aspect of the present invention, the plurality of first light sources may be laser diodes.

According to another aspect of the present invention, each of the plurality of first light sources may provide light with a wavelength different from each other.

According to another aspect of the present invention, each of the plurality of first light sources may form an irradiation axis which is angled with respect to the optical axis of the lens.

According to another aspect of the present invention, the plurality of first light sources may provide the light transmission circle with ultraviolet light and near-infrared light.

According to another aspect of the present invention, the head may include: a contact portion formed around the light transmission circle; and at least one electrode positioned on the contract portion.

According to another aspect of the present invention, the second light source may include a plurality of second light sources, wherein the plurality of second light sources may provide the light transmission circle with at least one of ultraviolet light, visible light, and near-infrared light.

According to another aspect of the present invention, the electronic device may further comprise a display on the body, wherein the display is configured to display user's skin indicator measured by the measurement unit.

According to another aspect of the present invention, the electronic device may further comprise a wireless communication unit installed in the body, the wireless communication unit may transmit the user's skin indicator to another electronic device.

Advantageous Effects

The effect of the electronic device according to the present invention will now be described.

According to at least one of the embodiments of the present invention, the condition of the user's skin can be measured appropriately, precisely or accurately.

According to at least one of the embodiments of the present invention, speckle imaging can be performed by providing laser light.

According to at least one of the embodiments of the present invention, the quality of the image for the skin measurement can be improved.

According to at least one of the embodiments of the present invention, it is possible to measure the skin condition of a user, to store or analyze information on the skin condition, and to provide care appropriate thereto.

According to at least one of the embodiments of the present invention, information about skin measurement can be shared with other electronic devices.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

MODE FOR INVENTION

Reference will now be made in detail to embodiments of the invention, examples of which are illustrated in the accompanying drawings. Wherever possible, the same reference numbers will be used throughout the drawings to refer to the same or like parts. In general, a suffix such as "module" and "unit" may be used to refer to elements or components. Use of such a suffix herein is merely intended to facilitate description of the specification, and the suffix itself is not intended to give any special meaning or function. It will be noted that a detailed description of known arts will be omitted if it is determined that the detailed description of the known arts can obscure the embodiments of the invention. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

The terms 'first', 'second', etc. may be used to describe various components, but the components are not limited by such terms. The terms are used only for the purpose of distinguishing one component from other components.

When an arbitrary component is described as "being connected to" or "being coupled to" another component, this should be understood to mean that still another component(s) may exist between them, although the arbitrary component may be directly connected to or directly coupled to another component. In contrast, when an arbitrary component is described as "being directly connected to" or "being directly coupled to" another component, this should be understood to mean that no component exists between them.

A singular expression can include a plural expression as long as it does not have an apparently different meaning in context.

In the present application, the terms "include" and "have" should be understood to be intended to designate that illustrated features, numbers, steps, operations, components, parts or combinations thereof exist and not to preclude the existence of one or more different features, numbers, steps, operations, components, parts or combinations thereof, or the possibility of the addition thereof.

Figure 1:
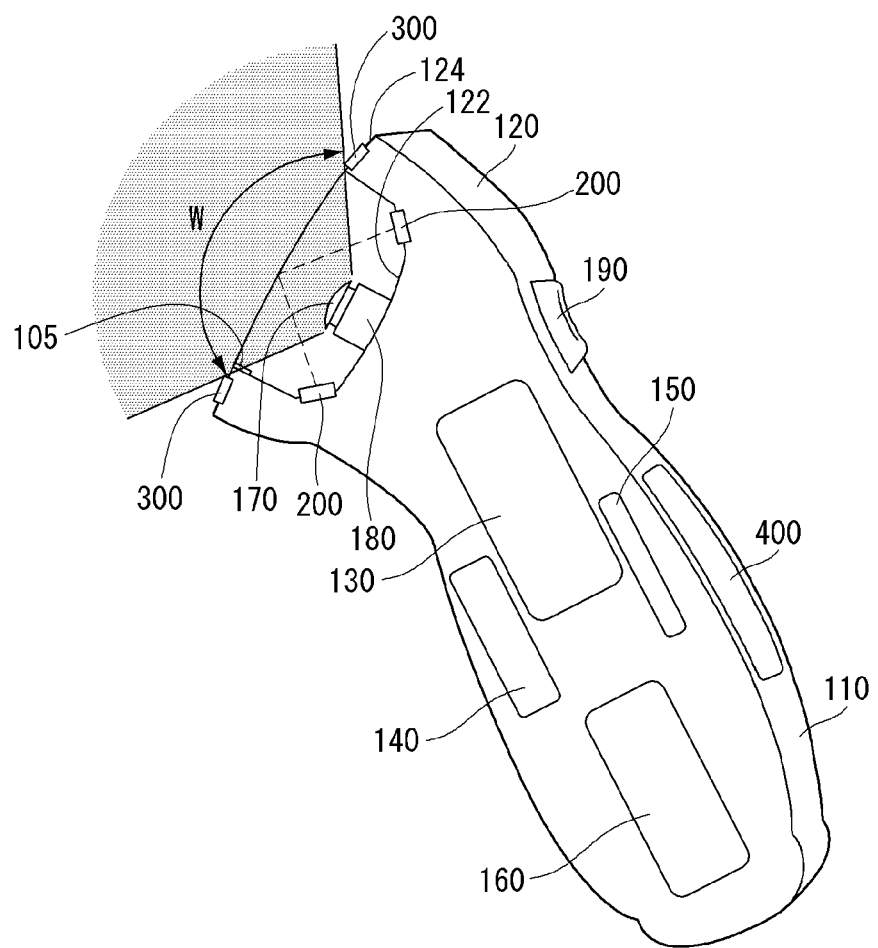
FIG. 1 shows an example of an electronic device according to an embodiment of the present invention.

FIG. 1 shows an example of an electronic device according to an embodiment of the present invention. FIG. 1 is a perspective view illustrating a body 110, a head 120, a PCB 130, a light controller 140, a wireless communication unit 150, a power supply unit 160, a lens 170 and a sensor 180, a light source 200, an electrode 300, a button 190, a display 400, and a reference chart 105.

The body 110 may have a convenient appearance for the user to grasp. Also, the body 110 may provide an internal space. The head 120 may extend from the body 110. The head 120 may be integrally formed with the body 110. Alternatively the head 120 may be separately formed and coupled to the body 110. The head 120 may have a recessed portion 122. Further, the head 120 may have a contact portion 124. The contact portion 124 may form the front surface of the head 120.

The PCB 130 may be mounted in the internal space of the body 110. Electronic elements required for an electronic device can be mounted on the PCB 130. The PCB 130 can control electronic components included in the electronic device.

The light controller 140 may be mounted in the internal space of the body 110. The light controller 140 can control the light source 200. For example, the light controller 140 may include a relay capable of adjusting a current supplied to the light source 200.

The wireless communication unit 150 can be capable of wireless communication with another electronic device. For example, the wireless communication unit 150 may be a module that enables communication such as Wi-Fi, BT, and NFC.

The power supply unit 160 may supply power to the electronic devices provided in the electronic device. The power supply unit 160 may be a secondary battery. For example, the power supply unit 160 may include a Li-ion battery.

The lens 170 may be provided in the recessed portion 122 of the body 110. The lens 170 may be a lens with wide angle w. The sensor 180 can receive external light through the lens 170 and convert the external light into an image. For example, the sensor 180 may includes a CMOS or a CCD.

The light source 200 may be provided in the head 120. The light source 200 may be provided in the recessed portion 122. The light source 200 may be located around the lens 170. The light source 200 may be provided in plural. The electrode 300 may be mounted on the contact portion 124 of the head 120. The electrode 300 may be provided in plural.

The button 190 may be located on the body 110. The button 190 may control the operation of the electronic device. For example, the user can press the button 190 to start skin measurement. For example, if the user presses the button 190 while the skin measurement is being continued, the skin measurement may be terminated.

The display 400 may be located on the body 110. The display 400 may display information such as the operation and status of the electronic device. The display 400 may include a touch screen. The touch screen can acquire the user's touch input.

The reference chart 105 may be located at the recessed portion 122 of the head 120. For example, the reference chart 105 may be RGB or Gray. The reference chart 105 may provide a reference for the image information obtained through the lens 170 and the sensor 180. For example, the image information may be a white balance, a color temperature, or the like.

Figure 2:
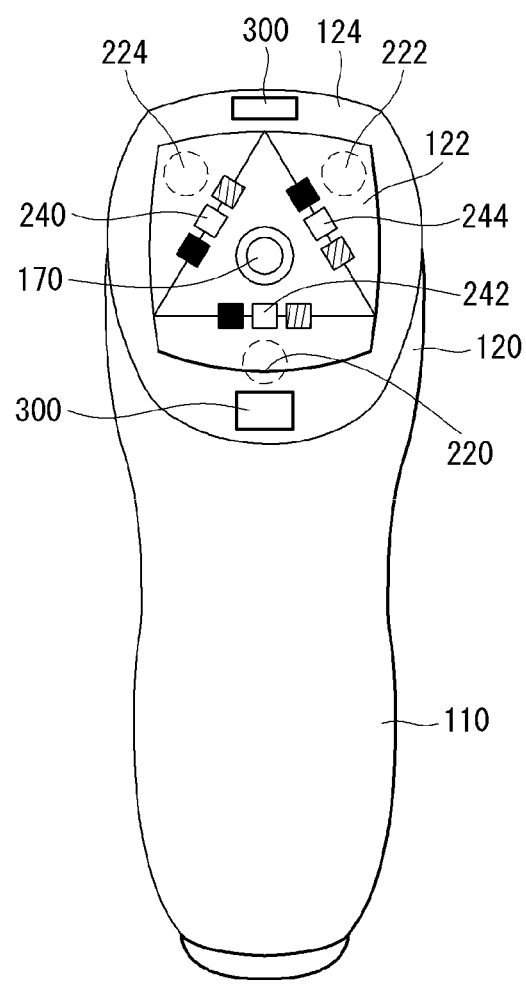
FIG. 2 shows an example of a front surface of the electronic device according to an embodiment of the present invention.
Figure 3:
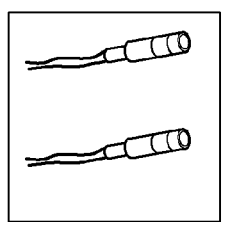
FIG. 3 shows an example of first and second light sources according to an embodiment of the present invention.
Figure 3:
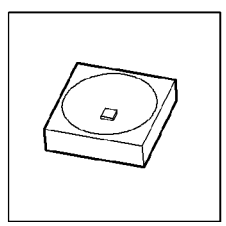
Figure 3:
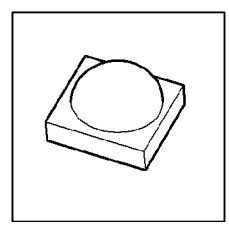
Figure 3:
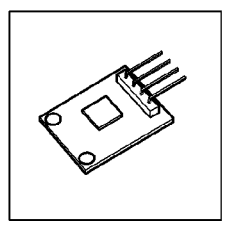
Figure 3:
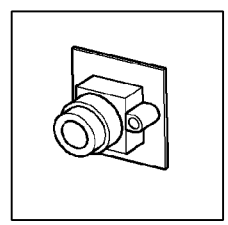

FIG. 2 shows an example of a front surface of the electronic device according to an embodiment of the present invention. FIG. 2 is a cross-sectional view illustrating a body 110, a head 120, a recessed portion 122, a contact portion 124, a first light source 220, a second light source 240, a lens 170 and an electrode 300. FIG. 3 shows an example of first and second light sources according to an embodiment of the present invention. FIG. 3 shows an example of the first and second light sources. FIG. 3 (a) shows a laser diode. FIG. 3 (b) shows a near-infrared LED. FIG. 3 (c) shows a ultraviolet LED. FIG. 3 (d) shows a visible light LED. FIG. 3 (e) shows a lens and a sensor.

In FIG. 2, the same reference signs are assigned to the same components as those described above, and a description thereof will be omitted. In the present specification, speckle imaging may mean a method of irradiating lights which have wavelengths different from each other on a subject and measuring the state of the surface (or interior adjacent o the surface) of the subject by using superimposition or interference.

The first light source 220 may be located at a corner or an outer periphery of the recessed portion 122. The first light source 220 may provide light for speckle imaging. The first light source 220 may provide light between ultraviolet and near-infrared rays (including ultraviolet and near-infrared region). For example, the wavelength of the first light source 220 may be any one of 450 nm, 530 nm, and 650 nm. For example, the first light source 220 may be a laser diode (LD). The first light source 220 may be in plural.

For example, the plurality of light sources 220 may be a red laser diode, a green laser diode, or a blue laser diode. The red laser diode 222 may provide light having a wavelength of 650 nm, the green laser diode 224 may provide light having a wavelength of 530 nm, and the blue laser diode 220 may provide light having a wavelength of 450 nm. In this embodiment, the two light sources 222, 224 among the plurality of first light sources 220, 222, 224 can be disposed at two corners of the recessed portion 122. The plurality of first light emitting sources 220, 222, and 224 may be disposed at positions corresponding to the vertices of the triangle.

The second light source 240 may be located between the lens 170 and the first light source 220, in the recessed portion 122. The second light source 240 may provide light for image acquisition. For example, the second light source 240 may provide ultraviolet light, visible light, or near-infrared light. For example, the second light source 240 may be a light emitting diode (LED). A plurality of the second light sources 240 may be one set, and a plurality of sets may be provided.

For example, one set of the second light sources 240 may include a red light source, a green light source, or a blue light source. Alternatively, one set of the second light sources 240 may provide a ultraviolet light, the visible light, and the near-infrared light. For example, one set of the second light sources 240 can provide light of the ultraviolet spectrum (405 nm) and the near-infrared spectrum (930 nm, 960 nm). In this embodiment of the present invention, three sets of the second light sources 240 can be disposed in the concave portion 122 such that the three sets are corresponding to a triangular as a whole.

The electrode 300 may be located at the contact 124. The electrode 300 can flow a electrical current. The electrical current on the electrode can be used to sense an object contacting the surface of the electrode 300.

For example, the electrode 300 may have a switching function. When the user touches the skin or the like with the electrode 300, the overall impedance of the circuit connected to the electrode 300 can be changed. Accordingly, the light provided by the first and second light sources 220 and 240 can be cut off. This can contribute to the improvement of the stability of the electronic device.

As another example, the electrode 300 may provide a skin measurement function. When the user's skin contact on the electrode 300, the impedance of the circuit connected to the electrode 300 can be changed. Accordingly, the electronic device can measure the skin condition of the user. For example, the skin condition may refer to the content of moisture, oil, and the like. The electrode 300 may improve the measurement precision of moisture and oil in the user's skin. The electrode 300 may be a plurality of electrodes in terms of electricity. For example, even if one electrode is observed with the naked eye, it may be electrically plural electrodes.

Figure 4:
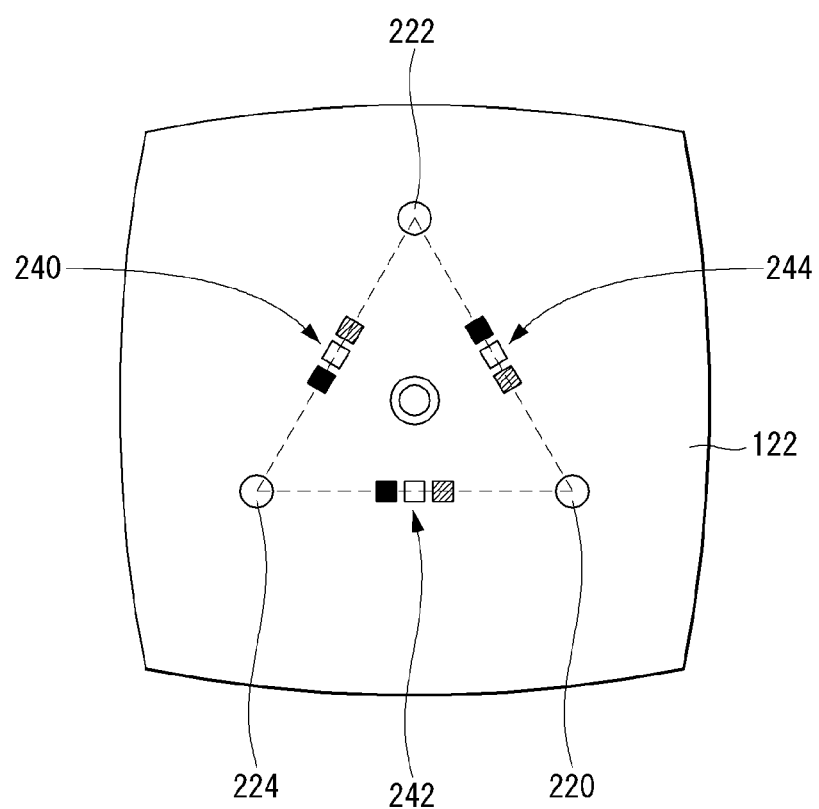
FIGS. 4 to 7 show examples of a head according to an embodiment of the present invention.

FIG. 4 shows another example of a head according to an embodiment of the present invention.

In this embodiment of the present invention, two of the plurality of first light sources 220 and 224 may be disposed at the two corners of the recessed portion 122. The plurality of first light sources 220, 222, and 224 may be disposed in the recessed portion 122 and may correspond to the vertices of a triangle. In this embodiment of the present invention, three sets 240, 242, and 244 of the plurality of second light sources may be disposed in the recessed 122 and may correspond to the triangle as a whole. Accordingly, the plurality of first and second light sources may be arranged along the triangle as a whole. The plurality of first light sources 220, 222, and 224 may correspond to the vertices of the triangle, and the plurality of second light sources 240, 242, and 244 may correspond to the sides of the triangle.

Figure 5:
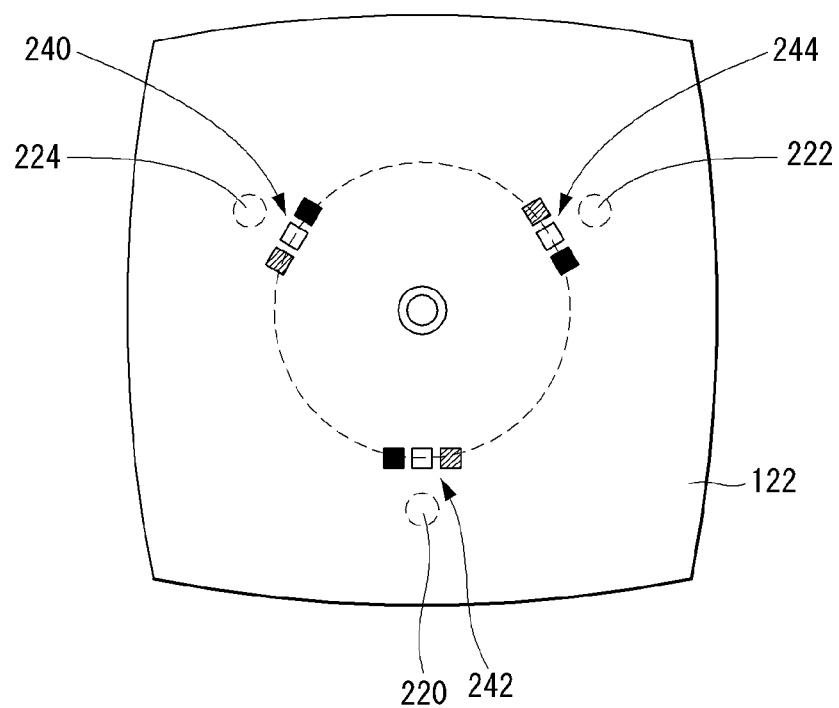

FIG. 5 shows another example of a head according to an embodiment of the present invention.

In this embodiment of the present invention, two among the plurality of first light sources 222 and 224 may be disposed at two corners of the recessed portion 122. The three first light sources 220, 222, and 224 may be located at the recessed portion 122 and may be disposed so as to correspond to the vertices of the triangle as a whole. In this embodiment of the present invention, the three sets 240, 242, 244 of second light sources may be disposed in the recessed portion 122 so as to form part of a circle or part of a triangle as a whole. Accordingly, the plurality of first and second light sources may be disposed so as to correspond to the vertices of the triangle as a whole. At this time, the plurality of first light sources 220, 222, and 224 may be disposed at the vertices of the triangle, and the plurality of second light sources 240, 242, and 244 may also be disposed at the vertices of the triangle.

Figure 6:
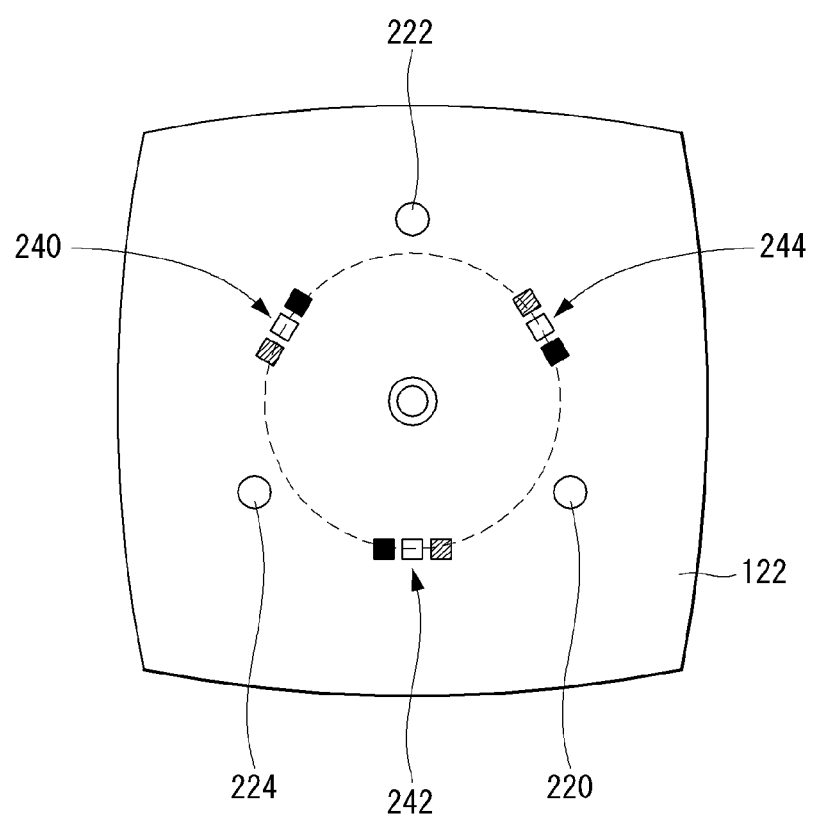

FIG. 6 shows another example of a head according to an embodiment of the present invention.

In this embodiment of the present invention, two of the plurality of first light sources 220 and 224 can be disposed at two corners of the recessed portion. The three first light sources 220, 222, and 224 may be disposed in the recessed portion 122 to form vertices of the triangle as a whole. In this embodiment of the present invention, three sets 240, 242, 244 of the plurality of second light sources may be disposed in the recessed portion 122 to form a part of a circle or part of a triangle as a whole. Accordingly, the plurality of first and second light sources may be arranged in a circular shape as a whole. Each of the plurality of first light sources 220, 222, and 224 may be disposed on the outside of the circular shape. Each of the plurality of second light sources 240, 242, and 244 may be disposed along the circular shape.

Figure 7:
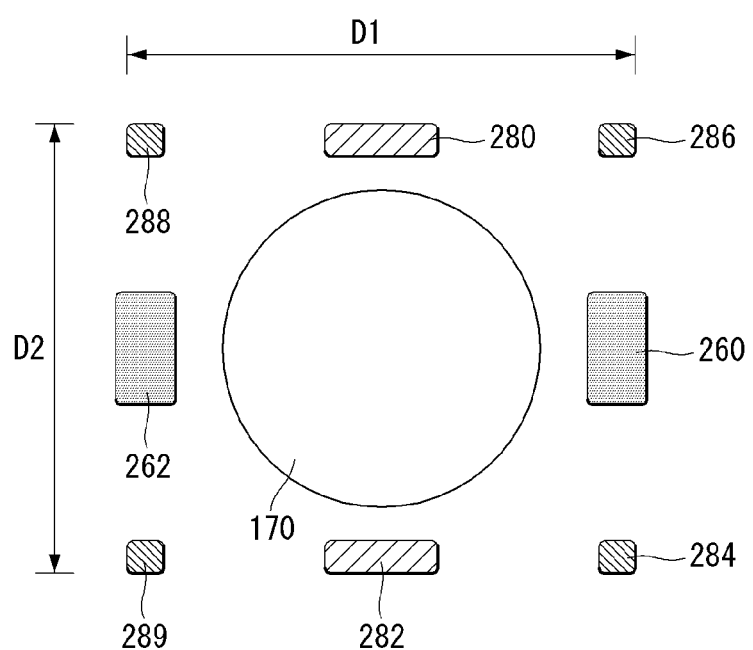

FIG. 7 shows another example of a head according to an embodiment of the present invention. FIG. 7 shows a plurality of first light sources 260, 262, a plurality of second light sources 280, 282, 284, 286, 288, 289, and a lens 170.

The plurality of first light sources 260 and 262 may provide light for speckle imaging. The plurality of first light sources 260 and 262 may provide light with a wavelength spectrum between a wavelength of ultraviolet and a wavelength of near-infrared rays (including ultraviolet and near-infrared). For example, the wavelength of the plurality of first light sources 260 and 262 may be any one of 450 nm, 530 nm, and 650 nm.

The plurality of first light sources 260 and 262 may be disposed on the left and right sides of the lens 170. For example, the first light source 260 may be disposed on the right side of the lens 170 and may provide light with 450 nm wavelength. As another example, the first light source 262 may be disposed on the left side of the lens 170 and may provide light with 650 nm wavelength.

The plurality of second light sources 280, 282, 284, 286, 288, 289 may be arranged on the upper and lower sides of the lens 170. For example, the first row of the second light sources 280, 286, 288 may be arranged on the upper side of the lens 170, and the second row of the second light sources 282, 284, 289 may be arranged on the lower side of the lens 170.

The light sources 280 and 282 may provide light or ultraviolet or near-infrared. For example, the light sources 280 and 282 may provide light with one of wavelength of 405 nm, 930 nm, and 960 nm. The light sources 284, 286, 288, 289 may provide a visible light.

The distance D1 may be, for example, 30 mm. The distance D2 may be 30 mm. The distances D1 and D2 may vary depending on the size of the head. In this embodiment of the present invention, the distances may be dependent on the size of the head and the angle to be described with reference to FIG. 8.

Figure 8:
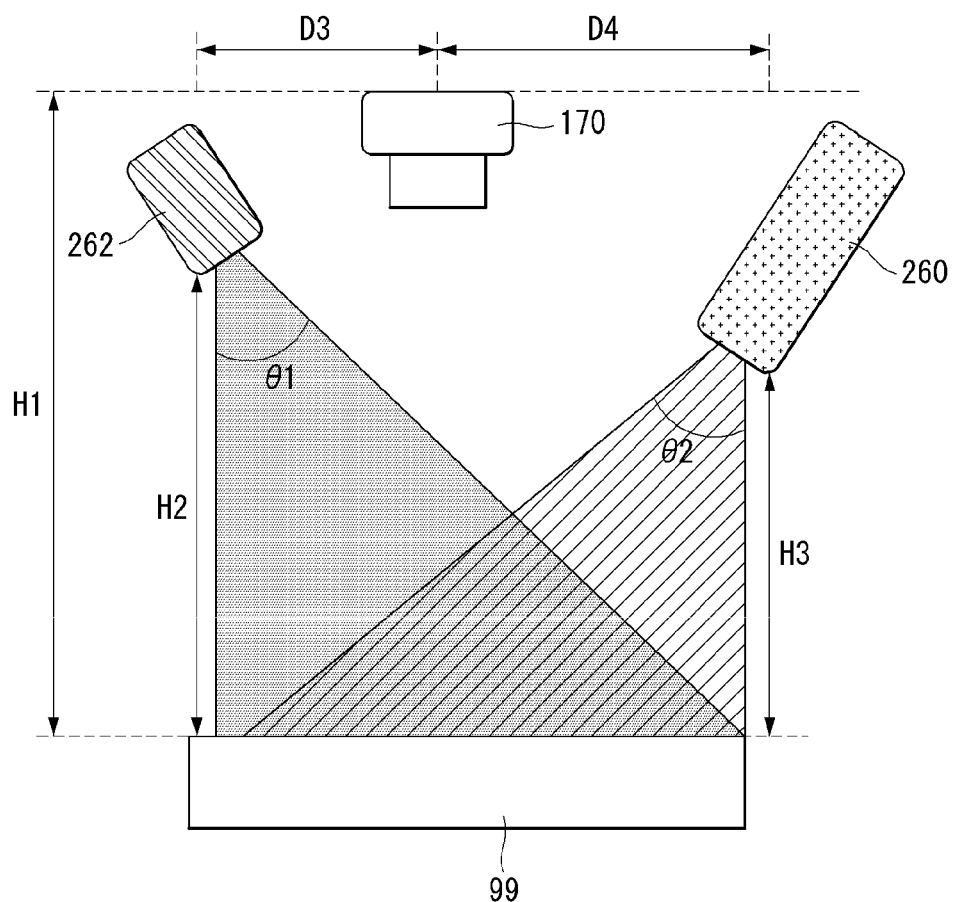
FIG. 8 shows an example of a light source and a lens according to an embodiment of the present invention.

FIG. 8 shows an example of a light source and a lens according to an embodiment of the present invention. FIG. 8 shows the light sources 260 and 262, the lens 170, and the subject 99.

The light sources 260 and 280 described with reference to FIG. 7 can be arranged as in FIG. 8.

The axis through which the lens 170 receives light can be defined as an optical axis, and the axis through which the light sources 260 and 262 irradiate light can be defined as an irradiation axis. The irradiation axis may be at a certain angle with respect to the optical axis. The light sources 260 and 262 may irradiate light along the irradiation axis and the irradiated light can be reflected upon the subject 99 and the reflected light can be used for measuring the state of the surface of the subject 99 (the surface may include not only the outer surface but also some depth). For example, the angle θ1 at which the light source 262 irradiates the subject 99 may be about 30 to 40 degrees. As a result, speckle imaging can be performed effectively. The angle θ2 at which the light source 260 irradiates the subject 99 may be about 30 to 40 degrees. Thus, irregular reflection of the subject 99 can be effectively reduced or suppressed.

The distance D4 between the lens 170 and the light source 260 may be 10 mm and the distance D3 between the lens 260 and the light source 262 may be 10 mm. The height H3 of the light source 262 may be 17 to 22 mm and the height H2 of the light source 262 may be 20 to 25 mm and the height H1 of the lens may be 25 to 30 mm.

Figure 9:
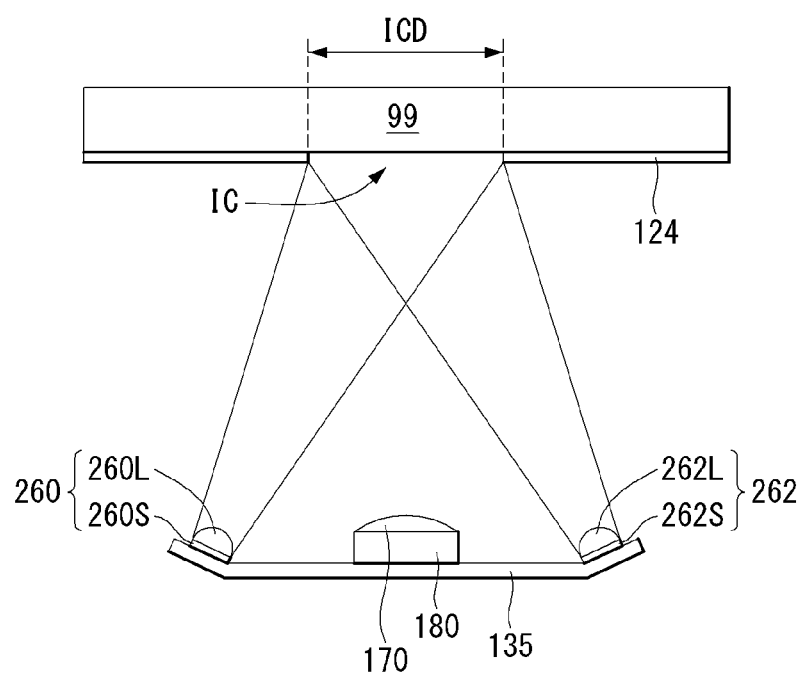
FIGS. 9 to 11 show examples of image measurement according to an embodiment of the present invention.
Figure 10:
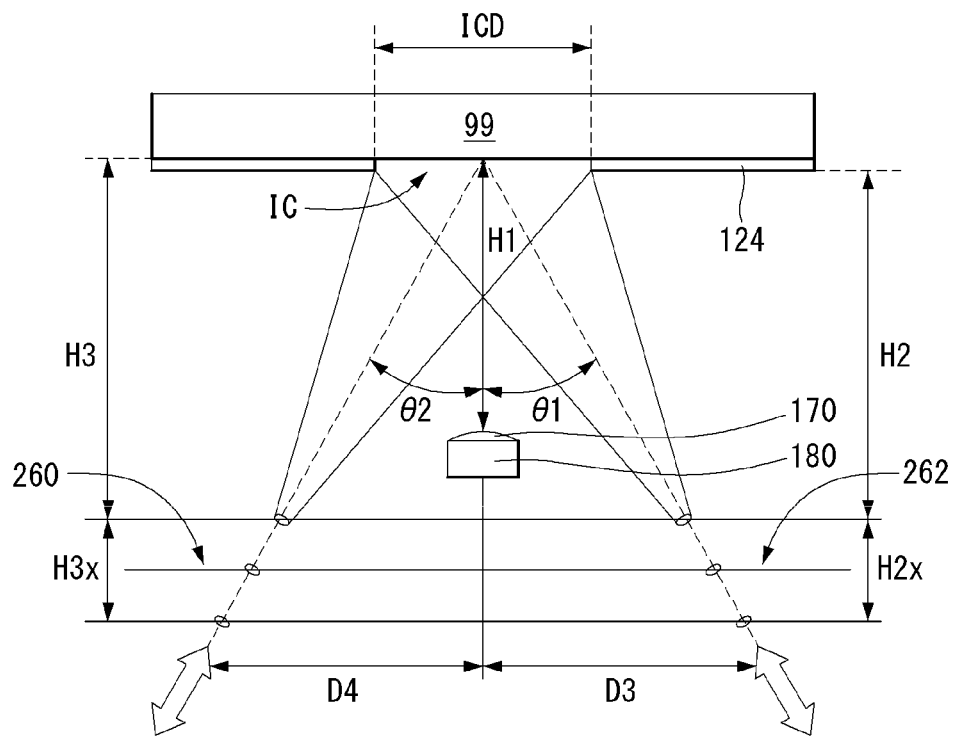
Figure 11:
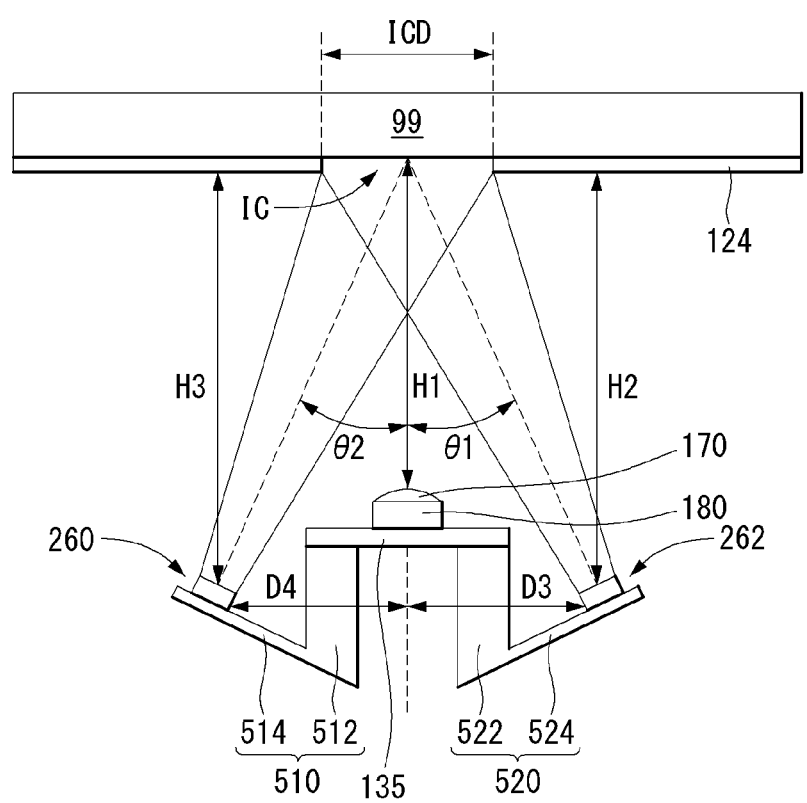

FIGS. 9 to 11 illustrate examples of image measurements according to an embodiment of the present invention.

Referring to FIG. 9, the image sensor 180 and/or the lens 170 may be mounted on the PCB 135. Further, the head 120 may have a light transmission circle IC. The light transmission circle IC may be formed on the head 120. The light transmission circle IC may be formed at the contact portion 124. The light transmission circle IC and the contact portion 124 can form the front surface of the head 120.

The image sensor 180 and/or the lens 170 may be directed to the light-transmission circle IC. That is, the lens 170 and the image sensor 180 can photograph the subject 99 which is in contact with the light-emitting circle IC. For example, the lens 170 may be a macro lens.

The first light sources 260 and 262 may be located around the lens 170. At this time, the first light sources 260 and 262 may be positioned forming an irradiation angle having a certain angle with respect to the optical axis of the lens 170.

The first light sources 260 and 262 may include light emitting devices 260S and 262S and lenses 260L and 262S. For example, the light emitting elements 260S and 262S may be LDs that provide light with wavelength of 405 nm or 650 nm. The lenses 260L and 262S can dissipate light provided by the light emitting elements 260S and 262S. In case that the light emitting elements 260S and 262S are LDs, light provided from the light emitting elements 260S and 262S may be closer to a collimated light. The collimation of light can be related to an angle of irradiation of light. For example, the light can be closer the collimated light as the irradiation angle of the light is small.

If the light emitting elements 260S and 262S provide light with a narrow radiation angle, light may not be provided all over the light transmission circle IC. Therefore, the light emitting elements 260S and 262S may be provided with the lens 170 in order to provide light on the entire light transmission circle IC.

The number of parts of the light emitting elements 260S and 262S including the lens 170 can be increased, and a precise process can be required, which may be difficult to miniaturize.

Referring to FIG. 10, the first light sources 260 and 262 may be located behind the image sensor 180 or the lens 170. The first light sources 260 and 262 can provide the light transmission circle IC with light. The first light sources 260 and 262 may include a plurality of light emitting elements 260 and 262. The plurality of light emitting elements 260 and 262 may include a first light emitting element 260 and a second light emitting element 262.

The image sensor 180 may be positioned at a certain distance H1 from the light transmission circle IC. The image sensor 180 may be located on the optical axis. The light transmission circle IC may have, for example, a diameter ICD of 10 to 12 mm. The image sensor 180 and/or the lens 170 may have an angle of view covering all the light transmission circle IC. For example, the distance H1 of the image sensor 180 to the light-transmission circle IC may be 25 to 30 mm, and the lens 170 may be a macro lens.

The first light emitting element 260 may be located on a side of the image sensor 180. The second light emitting element 262 may be located on another side of the image sensor 180. The first light emitting elements 260 and the second light emitting element 262 may be located on both sides of the image sensor 180.

The first light emitting element 260 may be positioned spaced apart from the image sensor 180 toward the left or right of the image sensor 180. The distance D4 may be between 13 and 15 mm. The irradiation axis of the first light emitting element 260 may form a certain angle θ2 with the optical axis of the image sensor 180. The angle θ2 formed by the irradiation axis of the first light emitting element 260 and the optical axis of the image sensor 180 may be 25 to 35 degrees. For example, the first light emitting element 260 may be an LD that provides light with a wavelength of 450 nm.

The first light emitting element 262 may be positioned spaced apart from the image sensor 180 toward the left or right of the image sensor 180. The distance D3 may be about 10 mm. The irradiation axis of the second light emitting element 262 may form a certain angle θ1 with the optical axis of the image sensor 180. The angle θ1 formed by the irradiation axis of the second light emitting element 260 and the optical axis of the image sensor 180 may be 25 to 35 degrees. For example, the second light emitting element 260 may be an LD that provides light with a wavelength of 650 nm.

The first light emitting element 260 may be located behind the image sensor 180. That is, the first light emitting element 260 may be located at the left or right rear side of the image sensor 180. The distance H3X by which the first light emitting element 260 is spaced rearward from the image sensor 180 may be a distance at which the light provided by the first light emitting element 260 maintains a certain or more output on the light transmission circle IC. For example, the light provided by the first light emitting element 260 can maintain an output of 1 mW on the light transmission circle IC.

The second light emitting element 262 may be located behind the image sensor 180. That is, the second light emitting element 262 may be located at the left or right rear side of the image sensor 180. The distance H2X by which the second light emitting element 262 is spaced rearward from the image sensor 180 may be a distance at which the light provided by the second light emitting element 260 maintains a certain or more output on the light transmission circle IC. For example, the light provided by the second light emitting element 262 can maintain an output of 1 mW on the light transmission circle IC.

The first light emitting element 260 and the second light emitting element 262 may be spaced rearward from the image sensor 180 and the first and second light emitting element 260 and 262 together can maintain an output of 1 mw or more on the light transmission circle IC.

Referring to FIG. 11, the base 135 may be located inside the head 120. The front surface of the base 135 can face the light transmission circle IC inside the head 120. The base 135 may be located on the optical axis of the lens 170. The base 135 may be spaced a certain distance H1 apart rearward from the light transmission circle IC. For example, the base 135 may include a PCB. For example, the base 135 may comprise a plate and a PCB mounted on the plate.

The image sensor 180 may be mounted on the base 135. The lens 170 covering the image sensor 180 may be mounted on the base 135.

The light source supporters 510 and 520 may be connected to the base 135, for example the light source supporters 510 and 520 may be connected to a rear surface of the base 135. In another aspect, the base 135 may be supported by the light source supporters 510 and 520. The light source supporters 510 and 520 may have a plurality of light source supporters 510 and 520. The plurality of light source supporters 510 and 520 may include a first light source supporter 510 and a second light source supporter 520. The description of the second light source supporter 520 is omitted in the same range as the first light source supporter 510.

The first light source supporter 510 may include a vertical portion 512 and an inclined portion 514. The vertical portion 512 may be located at the rear of the base 135. The vertical portion 512 may be positioned adjacent to the rear surface of the base 135. The vertical portion 512 may be fixed or contacted to the rear surface of the base 135. The vertical portion 512 may extend from the base 135 toward the rear of the base 135.

The inclined portion 514 may be connected to the vertical portion 512. An end of the vertical portion 512 can be connected to the base 135 and another end of the vertical portion 512 can be connected to the inclined portion 514. The inclined portion 514 may extend from the other end of the vertical portion toward away from the optical axis of the image sensor 180 and toward the contact portion 124.

The first light emitting element 260 may be positioned on the front surface of the inclined portion 514. The first light emitting element 260 may be spaced apart rearward from the base 135 by a distance D4 of 13 to 15 mm. The irradiation axis of the first light emitting element 260 may form a certain angle θ2 with the optical axis of the image sensor 180 and/or the lens 170. The front surface of the inclined portion 514 may be perpendicular to the irradiation axis of the first light emitting element 260. That is, the irradiation axis of the first light emitting element 260 may be a normal line of the front surface of the inclined portion 514.

The irradiation axis of the first light emitting element 260 can form a certain angle θ2 with the optical axis of the image sensor 180 and/or the lens 170, while the irradiation axis of the first light emitting element 260 may be not the normal line of the front surface of the inclined portion 14.

Figure 12:
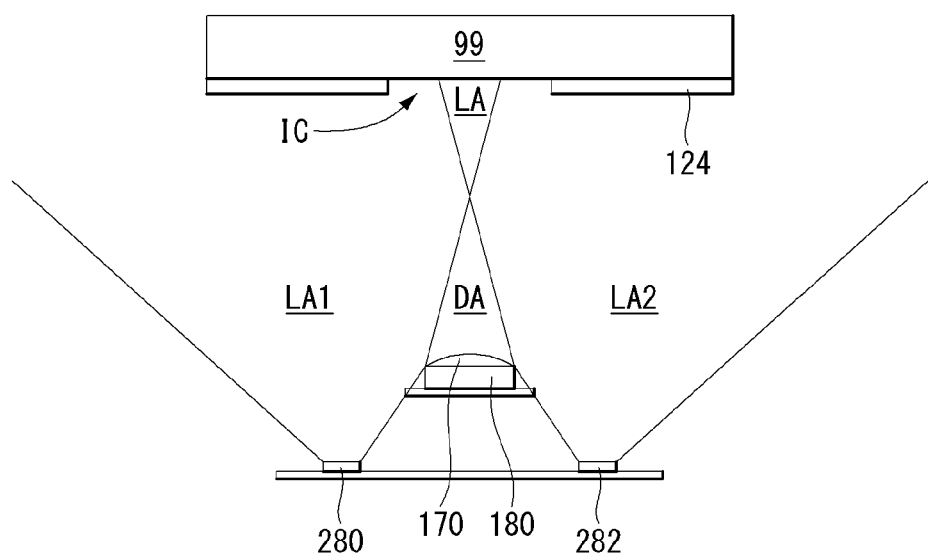
FIGS. 12 and 13 show other examples of image measurement according an embodiment of the present invention.
Figure 13:
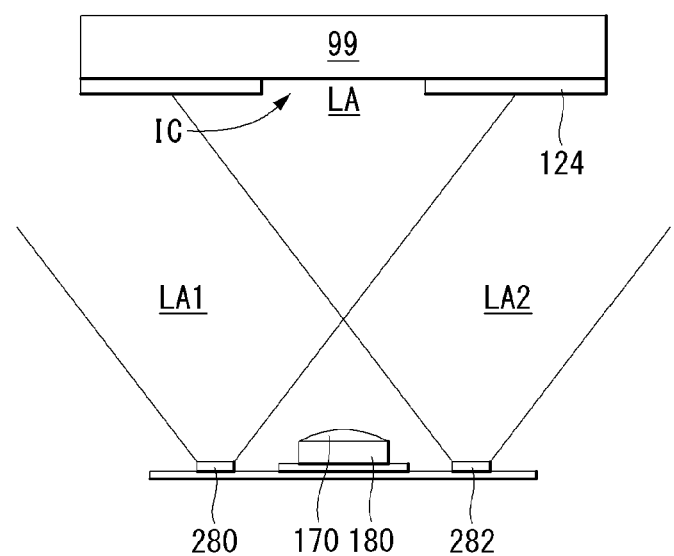

FIGS. 12 and 13 illustrate other examples of image measurements according to an embodiment of the present invention.

Referring to FIG. 12, the second light sources 280 and 282 may be located behind the image sensor 180 and/or the lens 170. The second light sources 280 and 282 may provide light toward the light transmission circle IC from the rear of the image sensor 180 and/or the lens 170. For example, the second light sources 280 and 282 may be LED devices.

The second light sources 280 and 282 may include a plurality of light emitting elements 280 and 282. The plurality of light emitting elements 280 and 282 may include a first light emitting element 280 and a second light emitting element 282.

The first light emitting element 280 may provide the light LA1 toward the light transmission circle IC. The second light emitting element 282 can provide light LA2 toward the light transmission circle IC. The light LA provided by the first light emitting device 280 and/or the second light emitting device 282 may be shielded by the image sensor 180 and/or the lens 170, a dark portion DA can be formed. The dark portion DA can degrade the quality of an image acquired through the light transmission circle IC.

Referring to FIG. 13, the second light sources 280 and 282 may be positioned side-by-side with the image sensor 180 and/or the lens 170. The second light sources 280, 282 may be either horizontal or slightly rearward relative to the lens 170. The second light sources 280 and 282 may include a plurality of light emitting elements 280 and 282. The plurality of light emitting elements 280 and 282 may include a first light emitting element 280 and a second light emitting element 282.

The first light emitting element 280 can provide the light LA1 toward the light transmission circle IC. The second light emitting element 282 can provide light LA2 toward the light transmission circle IC. The light provided by the first light emitting element 280 and/or the second light emitting element 282 may form a bright portion LA. This bright portion LA can improve the quality of the image acquired through the light transmission circle IC.

Figure 14:
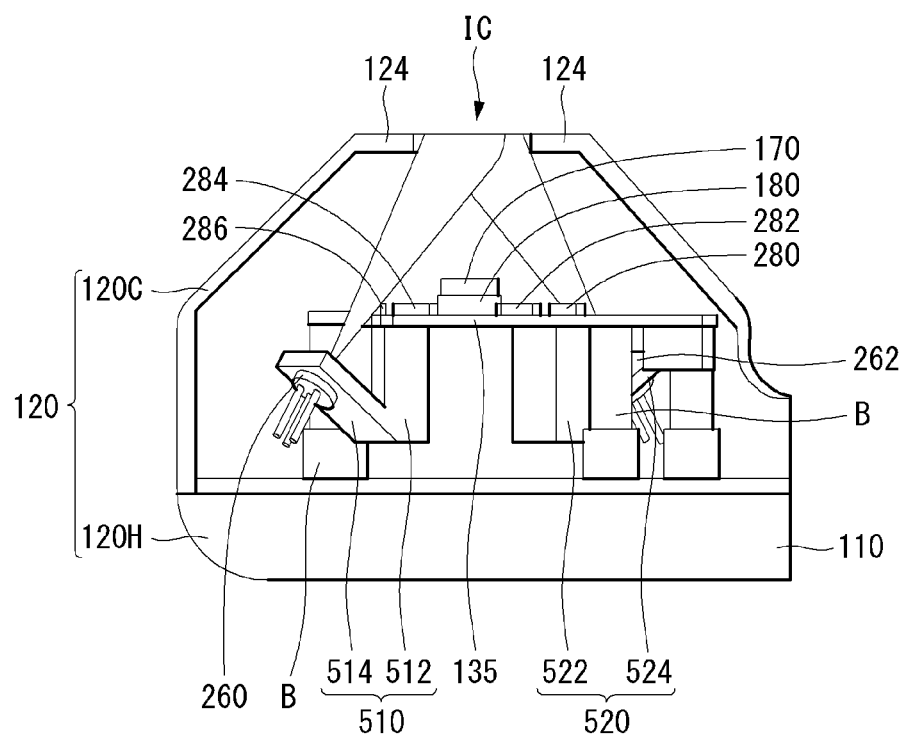
FIG. 14 shows another example of a light source and a lens according to an embodiment of the present invention.

FIG. 14 shows another example of a light source and a lens according to an embodiment of the present invention.

The head 120 may be formed at the body 110. The head 120 may provide an internal space for accommodation. The head 120 may include a rear cover 120H and a front cover 120C. A boss B may be formed in the head 120. The base 135 can be mounted inside the head 120 by a boss B. The light source supporters 510 and 520 may be formed on the rear surface of the base 135. The light source supporters 510 and 520 may include a plurality of the light source supporters 510 and 520. The plurality of light source supporters 510 and 520 may include a first light source supporter 510 and a second light source supporter 520.

The first light source supporter 510 may be positioned at a side of the base 135 and the second light source supporter 520 may be positioned at another side of the base 135. The plurality of light source supporter 510 and 520 may be positioned adjacent to the boss B. The height of the plurality of light source supporters 510 and 520 may be lower than the height of the boss B, with respect to the rear cover 120H.

The first light emitting element 260 of the first light sources 260 and 262 may be mounted on the first light source supporter 510. The second light emitting element 262 of the first light sources 260 and 262 may be mounted on the second light source supporter 520. The first light emitting element 260 and the second light emitting element 262 may provide light to the light transmission circle IC. The light provided to the light transmission circle IC can be the light for speckle imaging. That is, for example, the first light sources 260 and 262 may be LDs.

The image sensor 180 and/or the lens 170 may be located on the base 135. The second light sources 280, 282, 284, and 286 may be located around the image sensor 180 and/or the lens 170. The second light sources 280, 282, 284, and 286 may include a plurality of light sources 280, 282, 284, and 286. The plurality of light sources 280,282, 284, and 286 may be disposed around image sensor 180 and/or lens 170, along to any of the embodiments described above.

The second light sources 280, 282, 284, and 286 may provide light to the light transmission circles IC. For example, the second light sources 280, 282, 284, and 286 may be LEDs. The light provided to the light transmission circles IC by the second light sources 280, 282, 284, and 286 can improve the quality of the image of the object, wherein the image of the object can be adjacent to the light transmission circle IC.

Figure 15:
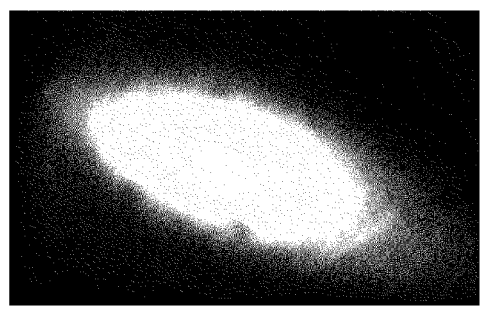
FIG. 15 shows an example of a measurement image according to an embodiment of the present invention.
Figure 15:
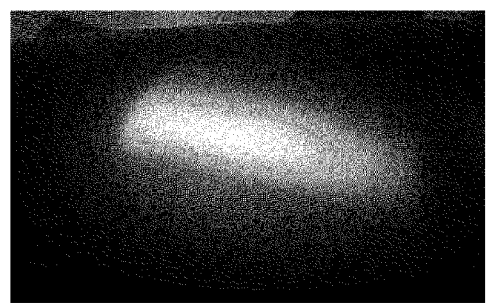
Figure 15:
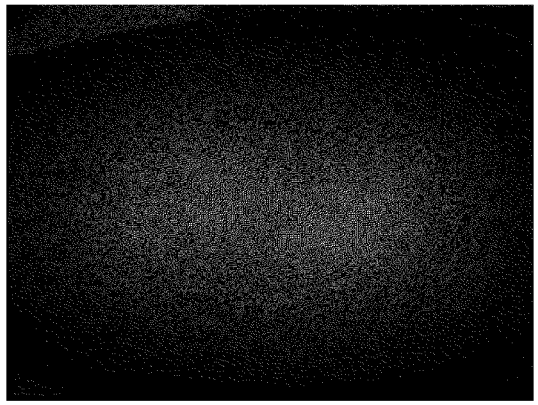
Figure 15:
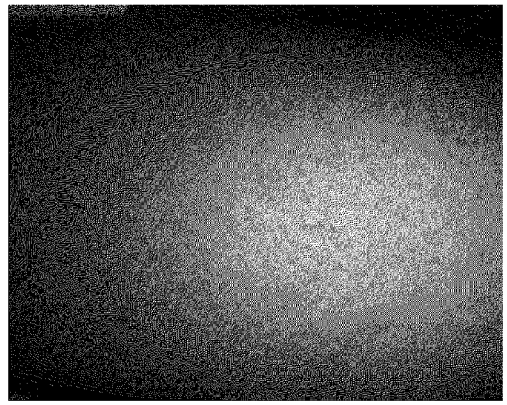

FIG. 15 shows an example of a measurement image according to an embodiment of the present invention. FIG. 15 (a) shows an example of a measurement image of a subject obtained by providing light of wavelength 405 nm, FIG. 15 (b) shows an example of a measurement image of a subject obtained by providing light of wavelength 650 nm, FIG. 15 (c) shows an example of a measurement image of a subject obtained by providing ultraviolet rays (UV), and FIG. 15 (d) shows an example of a measurement image of a subject obtained by providing visible light. FIGS. 15 (a) and (b) show speckle imaging and FIGS. 15 (c) and (d) show an image of a subject on which diffuse reflection can be removed. This may be an effect obtained by the configuration of FIG. 8, an effect obtained by the configuration of FIG. 14, or an effect obtained by other embodiments. More specifically, information about the condition of roughness, elasticity, oiliness, moisture, etc. of the user's skin can be obtained by the images shown in FIGS. 15 (a) and 15 (b). Information about the states of oil, moisture, pores, pigment, etc. of the user's skin can be obtained by the images shown in FIGS. 15 (c) and (d).

Figure 16:
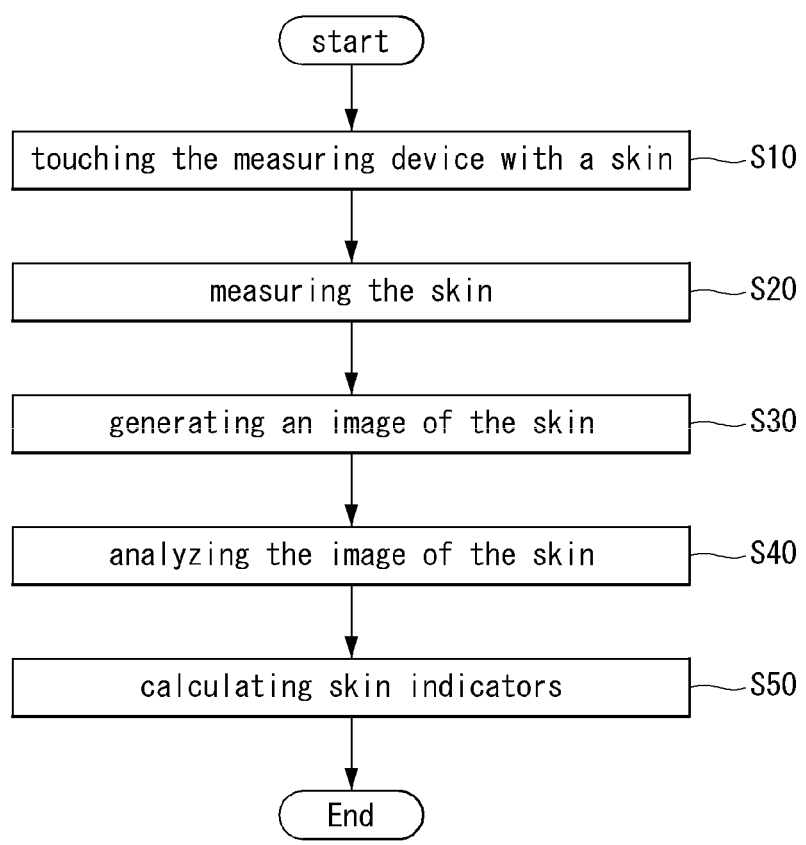
FIGS. 16 and 17 show examples of a skin measurement procedure according to an embodiment of the present invention.

FIG. 16 shows an example of a skin measurement procedure according to an embodiment of the present invention. In the following, description of the same constitution according to the same reference signs described above will be omitted.

The skin measurement procedure may include a step S10 in which the user touches the measuring device (previously described as an electronic device) with the skin. At this time, the electrode can be used to detect whether or not the measuring device contacts the skin. When the user presses the button, the measuring device can be operated. If the user presses the button and touches the measuring device with the skin, the measuring device may operate simultaneously with or after the skin touches. The skin measurement procedure may include a step S20 of measuring the user's skin condition. The skin measurement procedure may include a step S30 in which the first light source and the second light source provide light to the skin and the reflected light is received and an image can be generated. The skin measurement procedure may include a step S40 of analyzing the image. The skin measurement procedure may include a step S50 of calculating skin indicators based on skin condition analysis. Skin indicators can be, for example, roughness, elasticity, oil, moisture, pores, stains, hues, and the like.

Figure 17:
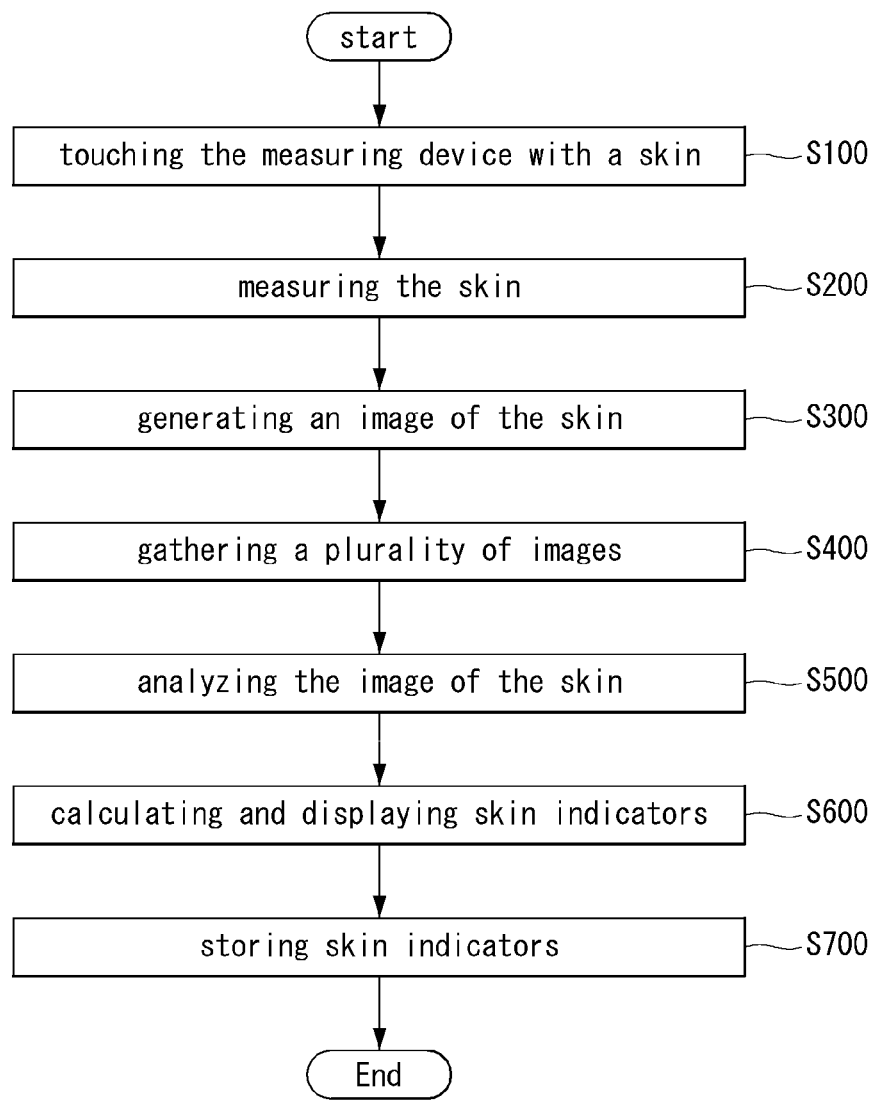

FIG. 17 shows an example of a skin measurement procedure according to an embodiment of the present invention. The skin measurement procedure may include a step S100 in which the user contacts the measuring device (previously described as an electronic device) with the skin. At this time, the electrode can be used to detect whether or not the measuring device contacts the skin. When the user presses the button, the measuring device can be operated. If the user presses the button and touches the measuring device with the skin, the measuring device may operate simultaneously with or after the skin touches. The skin measurement procedure may include a step S200 of measuring the skin condition of the user. The skin measurement procedure may include a step S300 in which the first light source and the second light source provide light to the skin and the reflected light is received and an image can be generated.

In this step S300, plurality of images can be generated. For example, image with 30 to 50 frames per second can be generated by light of 405 nm wavelength. For example, image with 30 to 50 frames per second can be generated by light of 650 nm wavelength. For example, image with 1 to 10 frames per second can be generated by ultraviolet LED, infrared LED, and visible LED. The skin measuring procedure may include a step S400 of gathering or merging the plurality of images. The skin measuring procedure may include a step S500 of analyzing the image of the skin, and a step S600 of calculating skin indicators and displaying the skin indicators. Skin indicators can be, for example, roughness, elasticity, oil, moisture, pores, stains, hues, and the like. The calculated skin indicators can be displayed in this step S600. The skin measuring procedure may include a step S700 of storing the skin indicators for the purpose of recording the user's history regarding skin condition.

Figure 18:
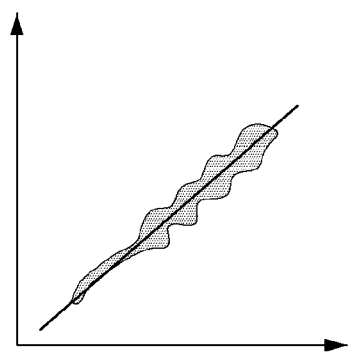
FIGS. 18 and 19 show examples of the result of the skin condition measurement according to an embodiment of the present invention.
Figure 18:
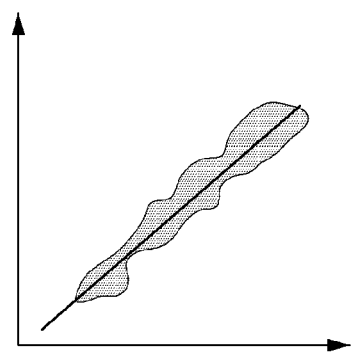
Figure 18:
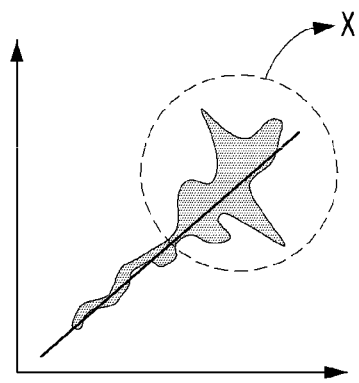
Figure 18:
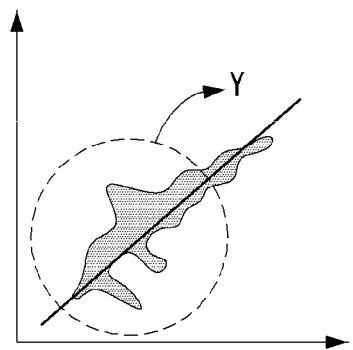
Figure 19:
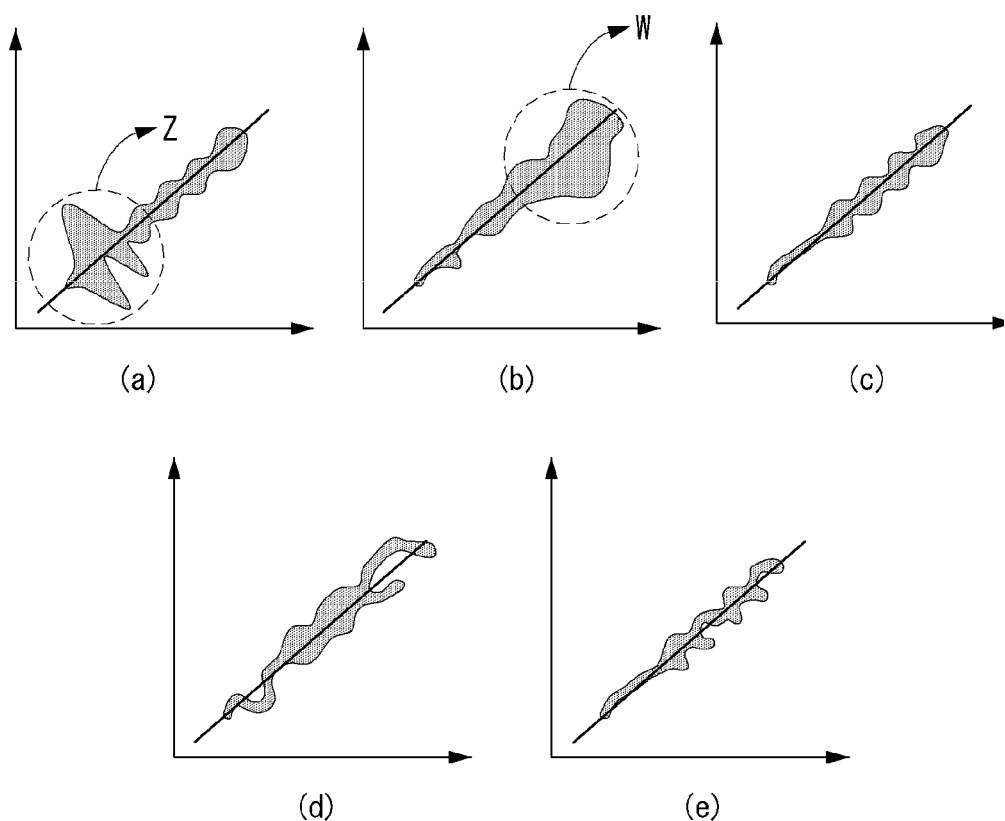

FIGS. 18 and 19 show examples of results of the skin condition measurement according to an embodiment of the present invention. More specifically, FIG. 18 shows an example of the result of the skin condition measurement by the first light source, and FIG. 19 shows an example of the result of the skin condition measurement by the second light source.

FIG. 18 (a) shows the distribution of roughness of the skin which is measured, FIG. 18 (b) shows the distribution of elasticity of skin which is measured, FIG. 18 (c) shows the distribution of oil of the skin which is measured, FIG. 18 (d) shows the distribution of moisture of the skin which is measured. The dispersion of the X region in FIG. 18 (c) and the Y region in FIG. 18 (d) should be noted. The accuracy of the measurement gets low, the dispersion of the distribution may gets higher.

FIG. 19 (a) shows the distribution of oil of the skin which is measured, FIG. 19 (b) shows the distribution of moisture of skin which is measured, FIG. 19 (c) shows the distribution of pores of the skin which is measured, FIG. 19 (d) shows the distribution of stains of the skin which is measured, FIG. 19 (e) shows the distribution of hue of the skin which is measured. The dispersion of the Z region in FIG. 19 (a) and the W region in FIG. 19 (b) should be noted. The accuracy of the measurement gets low, the dispersion of the distribution may gets higher.

Figure 20:
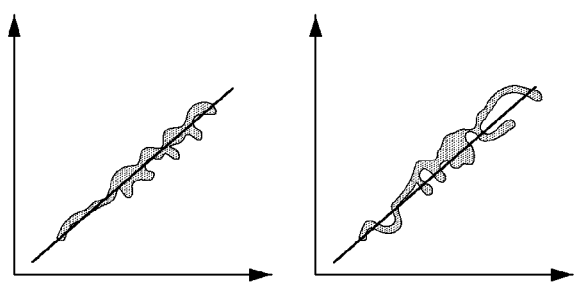
FIG. 20 shows other examples of measurement results of the skin condition according to an embodiment of the present invention.
Figure 20:
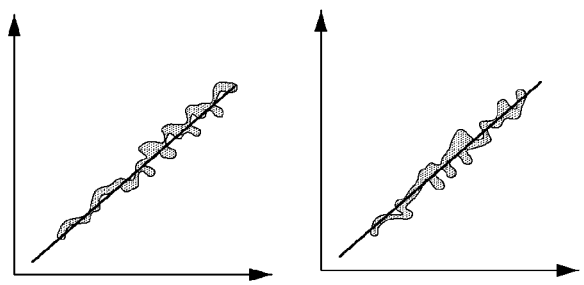
Figure 20:
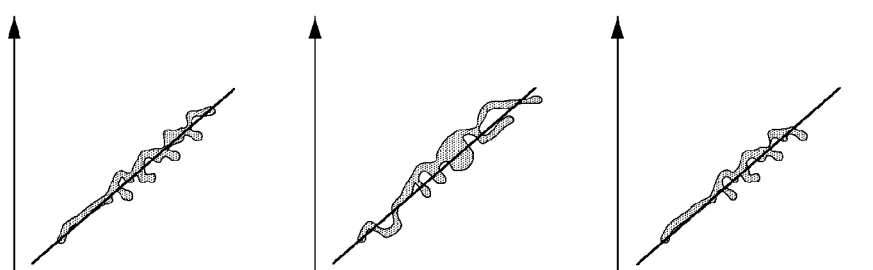

FIG. 20 shows other examples of measurement results of the skin condition according to an embodiment of the present invention.

FIG. 20 (a) shows the distribution of roughness of the skin which is measured, FIG. 20 (b) shows the distribution of elasticity of the skin which is measured, FIG. 20 (c) shows the distribution of oil of the skin which is measured, FIG. 20 (d) shows the distribution of moisture of the skin which is measured, FIG. 20 (e) shows the distribution of pores of the skin which is measured, FIG. 20 (f) shows the distribution of stains of the skin which is measured, FIG. 20 (g) shows the distribution of hue of the skin which is measured. It is noted that the distribution of all states of skin, especially the distribution of oil and moisture, is uniform. An even distribution can mean that the accuracy or precision of the measurement is high.

Figure 21:
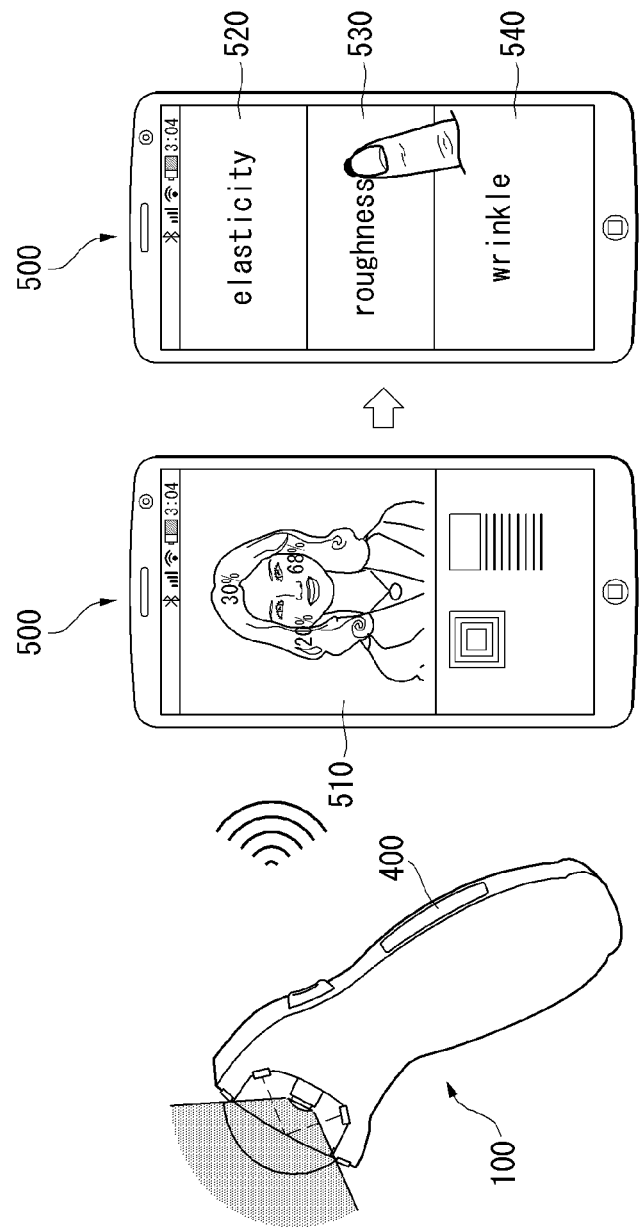
FIG. 21 shows an example of the use of an electronic device according to an embodiment of the present invention.

FIG. 21 shows an example of the use of an electronic device according to an embodiment of the present invention. FIG. 21 shows the electronic device 100 and another electronic device 500.

The electronic device 100 may communicate with another electronic device 500 via a wireless communication unit 150 (see FIG. 1). For example, the other electronic device 500 may be a mobile terminal. A skin care program can be installed in the mobile terminal. Referring to FIG. 21, an example of the user interface 510 of the skin care program. The user can measure the skin condition of the user using the electronic device 100, and then transmit the calculated and/or stored skin indicators to the mobile terminal 500. The mobile terminal 500 may transmit and store the indicator. The user can confirm his/her skin condition by using the mobile terminal 500. For example, a user can check an indicator 520 of elasticity, an indicator 530 of roughness, or an indicator 540 of wrinkles in his/her skin condition. On the other hand, the skin care program may be displayed on the display 400 of the electronic device 100 according to the present embodiment.

Figure 22:
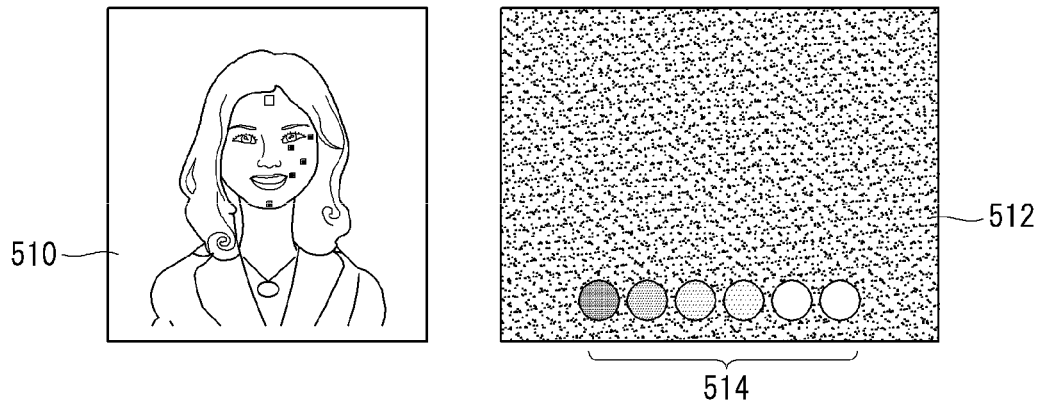
FIG. 22 shows an example of skin color correction according to an embodiment of the present invention.

FIG. 22 shows an example of skin color correction according to an embodiment of the present invention. FIG. 22 shows a user interface 510 and an image 512 on which a reference chart 514 is displayed.

In the portion described with reference to FIG. 1, a reference chart 514 can be represented in the image 512 simultaneously or later when measuring the user's skin. The user can select a portion of his/her face for measuring. For example, the skin condition of the forehead, the skin condition around the eyes, the skin condition of the cheek, or the skin condition around the mouth can be selected. The image 512 and the reference chart 514 for the selected portion may be displayed. Reference chart 514 may be, for example, Red, Green, Blue, or Gray scale. The image 512 measured can be corrected based on the color of the reference chart 514. As a result, it is possible to secure a more accurate color or hue image, and to improve the precision or accuracy of skin condition measurement.

Figure 23:
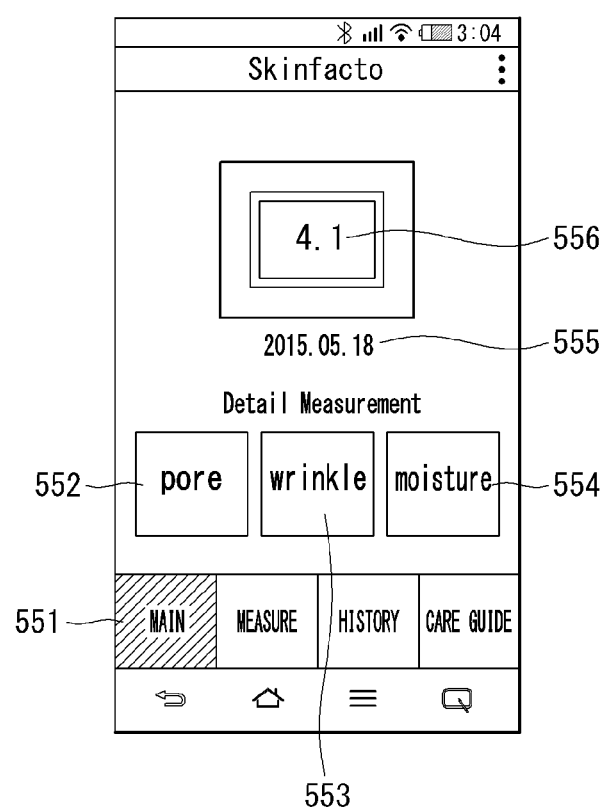
FIGS. 23 to 31 show examples of a user interface according to an embodiment of the present invention.

FIG. 23 shows an example of a user interface according to an embodiment of the present invention. FIG. 23 shows a main menu 551, a pore button 552, a wrinkle button 553, a moisture button 554, a measurement date 555, and a skin indicator 556.

The user can select one of the pore button 552, the wrinkle button 553, and the moisture button 554, after touching the main menu 551. On the other hand, the user interface can display the measurement date 555. In addition, the user interface may display the skin indicator 556 measured on the date of the measurement date 555. The skin indicator 556 may be an entire skin indicator of the user's skin, or may be a skin indicator of each pore, wrinkles, moisture, and the like. The skin indicator 556 may be an index representing a relative state with respect to a certain criterion, or an index representing an absolute value.

FIGS. 24 to 31 show other examples of the user interface according to an embodiment of the present invention. The main menu 551, the pore button 552, the wrinkle button 553, the moisture button 554, the pore indicator 552a, the wrinkle indicator 553a, the moisture indicator 554a, the elasticity indicator 557, the elasticity indicator 558, the elasticity indicator 557a, the oil indicator 558a, and the like can be displayed on the user interface.

Figure 24:
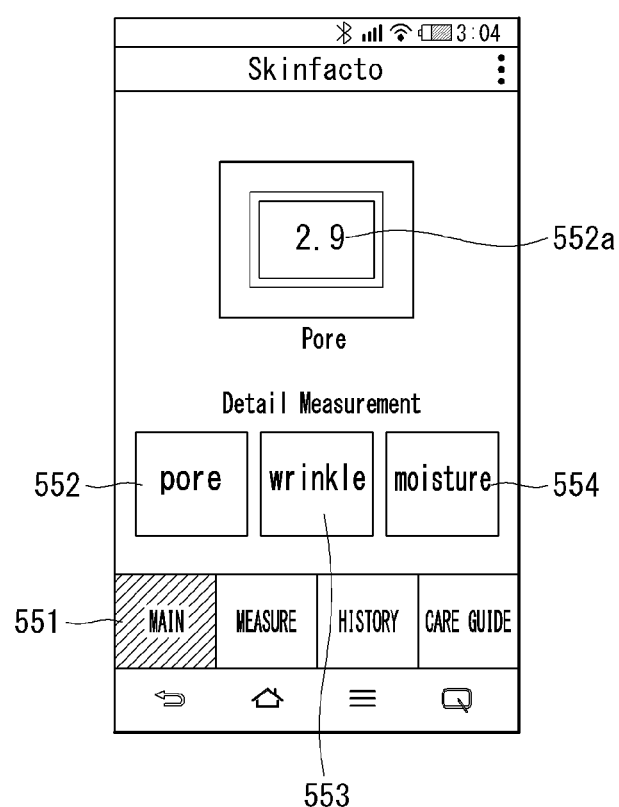
Figure 25:
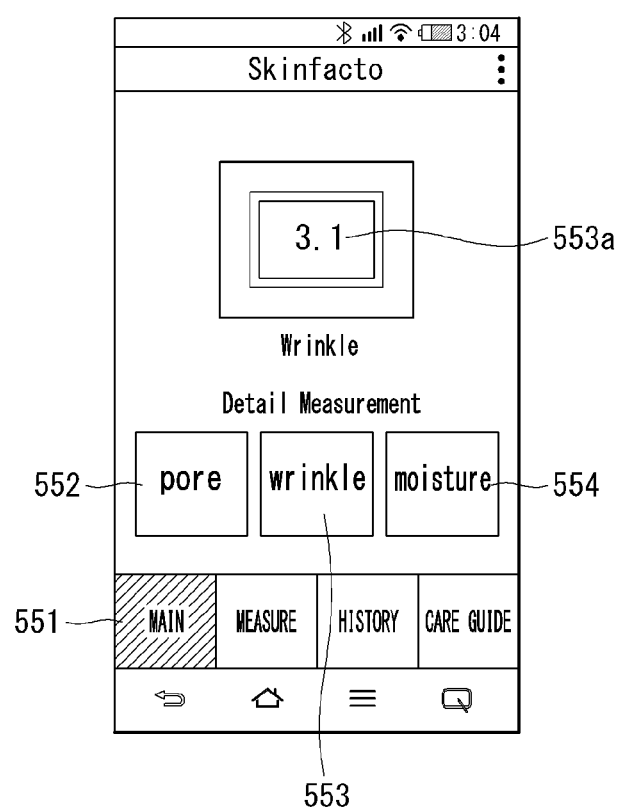
Figure 26:
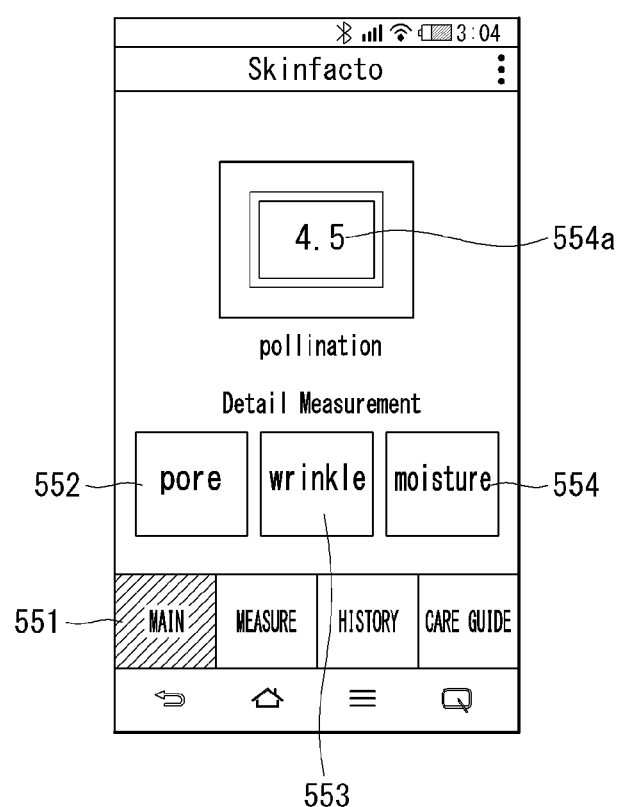
Figure 27:
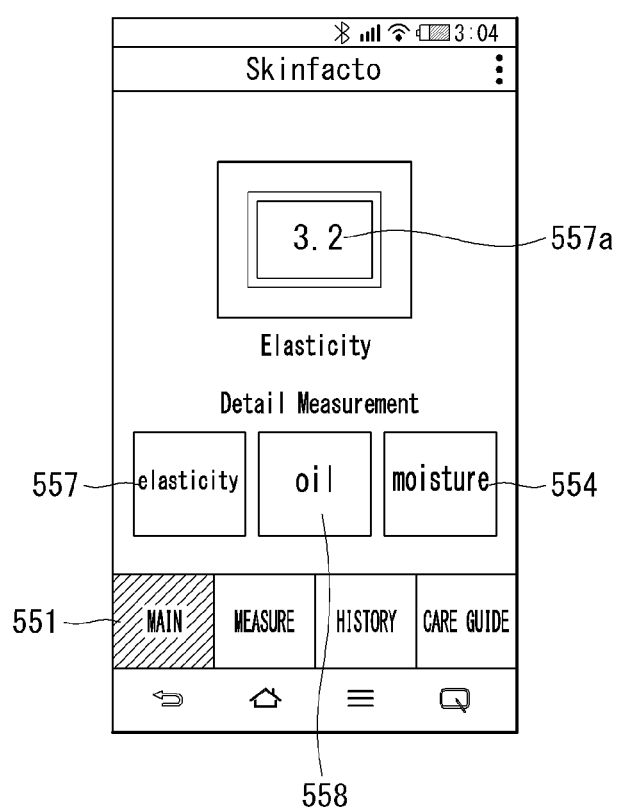
Figure 28:
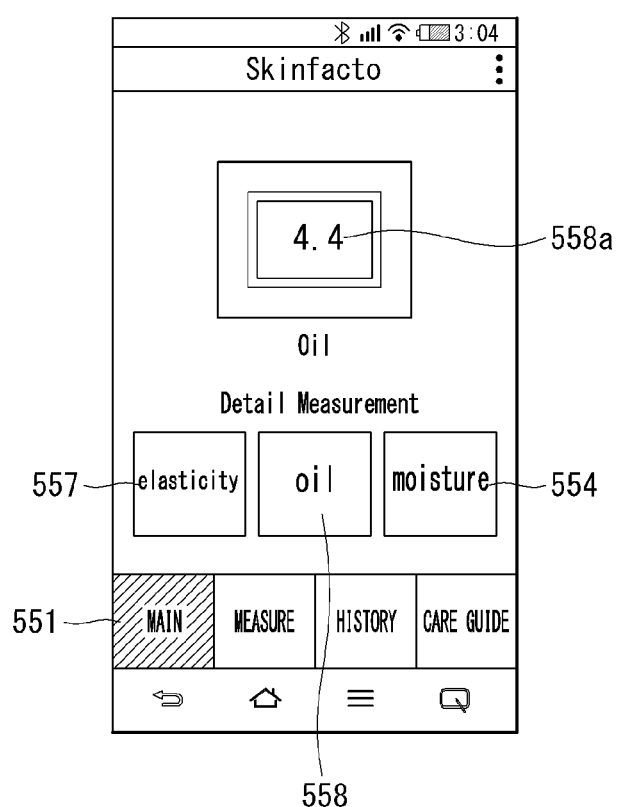

Referring to FIG. 24, the user can select the pore button 552 to check the status of the pore. When the pore button 552 is selected, the interface can display the user's pore indicator 552a. Referring to FIG. 25, the user can check the wrinkle state by selecting the wrinkle button 553. When the wrinkle button 553 is selected, the interface can display the wrinkle indicator 553a. Referring to FIG. 26, the user can check the state of moisture by selecting the moisture button 554. When the moisture button 554 is selected, the interface can display the moisture indicator 554a. Referring to FIG. 27, the user can check the state of elasticity by selecting the elasticity button 557. When the elasticity button 557 is selected, the interface can display the elasticity indicator 557a. Referring to FIG. 28, the user can select the oil button

558 to check the state of the oil. If the user selects the oil button 558, the interface can display the oil indicator 558a.

Figure 29:
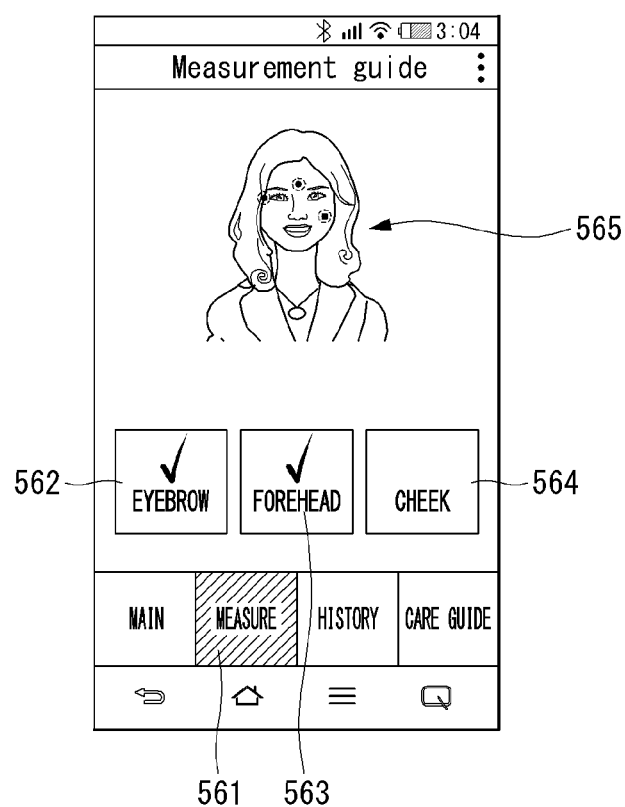

FIG. 29 shows another example of a user interface according to an embodiment of the present invention. FIG. 29 shows the measurement menu 561, the eyebrow button 562, the forehead button 563, the cheek button 564, and the measurement spot 565.

When the user selects the measurement menu 561, the interface can provide a skin measurement guide to the user. When the eyebrow button 562 is selected, the measurement spot 565 in the eyebrow can be displayed. When the forehead button 563 is selected, the measurement spot 565 in the forehead can be displayed. When the cheek button 564 is selected, the measurement spot 565 in the cheek can be displayed. Accordingly, the user can easily recognize the measurement spot 565 for measuring the skin using the electronic device of this embodiment.

Figure 30:
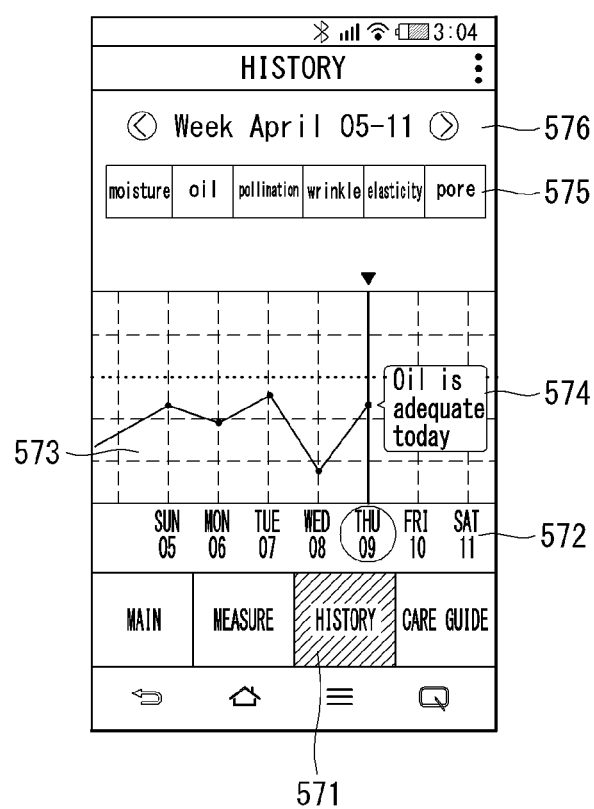

FIG. 30 shows another example of a user interface according to an embodiment of the present invention. FIG. 30 shows a history menu 571, a measurement date 572, a skin indicator 573, a skin condition 574, a item list 575, and a date of interest 576.

When the user selects the history menu 571, the interface may display a history associated with the user's skin measurement. The history can display the measurement date 572 on the horizontal axis and the skin indicator 573 on the vertical axis. The history on one of the item list 575 can be displayed. When the user selects any one of moisture, oil, wrinkles, elasticity, pores, and the like in the item list 575, the interface can display a history of the selected item. The skin indicator 573 may be displayed in a qualitative state as well as in a quantitative value. The skin condition 574 may indicate a qualitative condition of the selected skin condition. The day of interest 576 may indicate a certain day on which the user measured the skin. Users can also view by week, month, and year.

Figure 31:
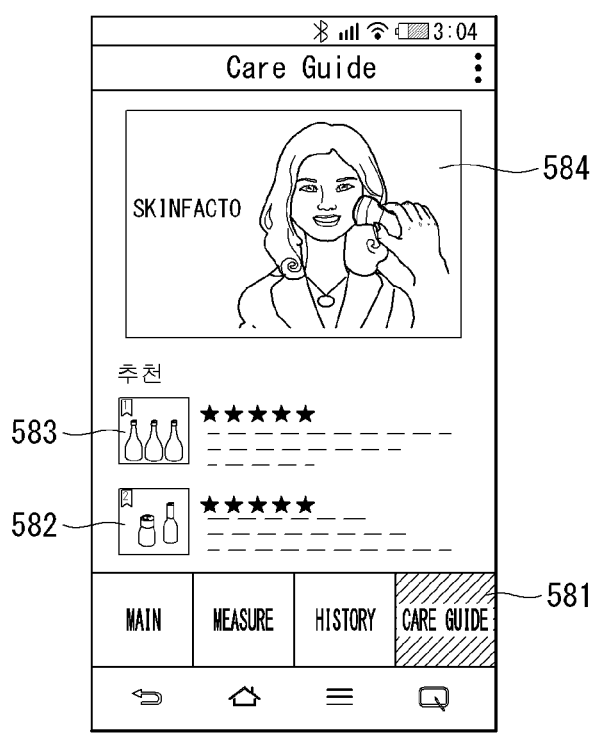

FIG. 31 shows another example of a user interface according to an embodiment of the present invention. FIG. 31 shows a care guide screen 581, recommendation items 582, 583, and an advertisement 584.

According to the measured skin condition of the user, a product suitable for the user's skin or a necessary product can be displayed on the interface. When the user selects the care guide menu 581, the interface may display recommendation items 582,583 which are suitable for the user's skin or necessary. The recommendation items 582,583 may be, for example, a kind of cosmetics. The recommendation items 582,583 can also display the ingredients needed for the user's skin. The interface may display advertisement 584. The advertisement 584 may be an advertisement for the user when selecting one of the recommendation items 582 and 583, or may be an advertisement provided at random. Recommendation items 582,583 may be linked to advertisements of the product or provide a store location where the product is sold. In addition, dermatology can be recommended depending on the skin condition of the user.

Certain embodiments of the invention described above or other embodiments are not mutually exclusive or distinct from each other. Any or all of the embodiments of the invention described above may be combined or combined with each other.

It will be apparent to persons skilled in the art that the present invention may be embodied in other specific forms without departing from the spirit or essential characteristics thereof. The above detailed description should not be construed in all aspects as limiting and should be considered illustrative. The scope of the present invention should be determined by rational interpretation of the appended claims, and all changes within the scope of equivalents of the present invention are included in the scope of the present invention.

The invention claimed is:

1. An electronic device comprising:
    a body;
    a head extended from the body, the head including an internal space for accommodating;
    a light transmission circle formed on the head; and
    a measurement module installed in the internal space of the head,
    wherein the measurement module includes:
    a plurality of first light sources providing the light transmission circle with light for speckle imaging;
    an image sensor positioned between the light transmission circle and the plurality of first light sources, the image sensor being spaced apart from the plurality of first light sources; and
    a lens covering the image sensor, the lens being positioned between the image sensor and the light transmission circle,
    wherein the light transmission circle passes light emitted from the plurality of first light sources to an object and reflected from the object to the measurement module,
    wherein the plurality of first light sources include at least three first light sources and two of the at least three first light sources are each disposed at two corners in the internal space and one of the at least three first light sources is disposed between the two of the at least three first light sources, and
    wherein the at least three first light sources are disposed around the image sensor in a triangular shape when viewed from the front of the electronic device so that each of the at least three first light sources corresponds to each vertice of a triangle.

2. The electronic device of claim 1, further comprising a second light source providing the light transmission circle with light for photographing an image.

3. The electronic device of claim 2, wherein the second light source includes a plurality of second light sources, and
    wherein the plurality of second light sources provide the light transmission circle with at least one of ultraviolet light, visible light, and near-infrared light.

4. The electronic device of claim 1, wherein the plurality of first light sources are laser diodes.

5. The electronic device of claim 1, wherein each of the plurality of first light sources provide light with a wavelength different from each other.

6. The electronic device of claim 1, wherein each of the plurality of first light sources forms an irradiation axis which is angled with respect to an optical axis of the lens.

7. The electronic device of claim 1, wherein the plurality of first light sources provide the light transmission circle with ultraviolet light and near-infrared light.

8. The electronic device of claim 1, wherein the head includes:
    a contact portion formed around the light transmission circle; and
    at least one electrode positioned on the contract contact portion.

9. The electronic device of claim 1, further comprising a display on the body, wherein the display is configured to display user's skin indicator measured by the measurement module.

10. The electronic device of claim 1, further comprising a wireless communication unit installed in the body, wherein the wireless communication unit transmits the user's skin indicator to another electronic device.

* * * * *